(12) United States Patent
Linsen et al.

(10) Patent No.: US 6,901,334 B2
(45) Date of Patent: May 31, 2005

(54) METHODS AND SYSTEMS FOR HIGH THROUGHPUT ANALYSIS

(75) Inventors: Michael William Linsen, North Wales, PA (US); Edward Albert Schmitt, Richboro, PA (US); Mark Richard Schure, Blue Bell, PA (US)

(73) Assignee: Rohm and Haas Company, Philadelphia, PA (US)

( * ) Notice: Subject to any disclaimer, the term of this patent is extended or adjusted under 35 U.S.C. 154(b) by 146 days.

(21) Appl. No.: 10/307,654

(22) Filed: Dec. 2, 2002

(65) Prior Publication Data

US 2003/0125884 A1 Jul. 3, 2003

Related U.S. Application Data

(60) Provisional application No. 60/339,903, filed on Dec. 17, 2001.

(51) Int. Cl.[7] .............................................. G01N 32/00
(52) U.S. Cl. .............................. 702/22; 702/22; 702/30; 702/182; 702/189; 422/211; 422/131; 423/213.2; 423/230; 502/103; 502/118; 568/478
(58) Field of Search ............................... 702/22, 30–32, 702/182, 189; 422/211, 131; 423/213.2, 230; 502/103, 117; 568/478, 68

(56) References Cited

U.S. PATENT DOCUMENTS 6,149,882 A  11/2000 Guan et al.
6,592,822 B1 * 7/2003 Chandler ................. 422/82.05
2002/0197725 A1 * 12/2002 Eaton et al. ................ 436/104
2003/0224927 A1 * 12/2003 Shih .......................... 502/103

FOREIGN PATENT DOCUMENTS

WO       WO0166245 A2    9/2001

OTHER PUBLICATIONS

Wilson et al., 'Stationary Power Applications for Polymer Electrolyte Fuel Cells', Dec. 1996, IEEE Article, pp. 107–112.*

ABB, 'Technology frontiers in the downstream business', Mar. 2001, Synergy, pp. 8–11.*

Tobias, 'Adaptive Process Control of an Acetic Acid Reactor', Dec. 1997, Adaptive Resources, pp. 45–49.*

* cited by examiner

*Primary Examiner*—Marc S. Hoff
*Assistant Examiner*—Elias Desta

(57) ABSTRACT

Methods of analyzing processes for making catalysts and/or certain properties of catalysts using a plurality of reaction zones are provided. The methods of the present invention have the capability to define and execute, in rapid succession, a plurality of experiments under disparate reaction conditions. An operator may define and execute a plurality of experiments on user-defined quantities of disparate catalysts, using user-defined input feeds, residence times, and temperature profiles.

21 Claims, 10 Drawing Sheets

Fig. 7

Crate 1 Sample Logon Form

Submitter ID: RSOUMS ▼  Study Name: New Route ▼  Create Study

Study Description (read only): Make a / This is a

Cell Contents:

| Submitter ID | Study Name | Sample Name* | Mass (g) | Height (cm) | Res. Time (s) | Sample Description |
|---|---|---|---|---|---|---|
| RSOUMS | New Route | | 2.00 | 4.00 | 5.00 | Blank |
| RSOUMS | New Route | S1 | 2.00 | 4.00 | 5.00 | The enhanced Schurium catalyst |
| RSOUMS | New Route | S2 | 1.70 | 4.00 | 5.00 | The enhanced Schmuttium catalyst |
| RSOUMS | New Route | S3 | 1.85 | 4.00 | 5.00 | The enhanced Schillerium catalyst |
| RSOUMS | New Route | S4 | 1.88 | 4.00 | 4.00 | The enhanced Linsenium catalyst |
| RSOUMS | New Route | S5 | 2.10 | 4.00 | 4.00 | Sprinkled with Lamola dust |
| | | | | | | |

* Enter "Blank" in sample position 1 for Background mode 3. Do not enter "Blank" in other sample positions.

Current Temperature Method is:

(None)

| Assign/Change Temperature Method | Help |
|---|---|
| Exit Program | Print Sample Info. |
| | Continue |

Fig. 8

Crate 1 Temp Program Input Form

Temperature Ramp Specification
Note all times in Minutes

| | °C/min | Next°C | Hold Time | Run Time |
|---|---|---|---|---|
| Initial | | 35 | 1 | |
| Range 1 | 1 | 40 | 5 | |
| Range 2 | 5 | 100 | 10 | |
| Range 3 | 5 | 400 | 10 | |
| Range 4 | | | | |
| Range 5 | | | | |

| Cancel | Help | Apply and Save method | Apply but Don't Save |

Fig. 9

Crate 1 Flow Control

Flow and Sample Control

| Controller | Enter Flow in CC/Min | Present Reading in CC/min |
|---|---|---|
| 1 | 11.54 | 11.65 |
| 2 | 11.54 | 0.00 |
| 3 | 11.54 | 0.26 |
| 4 | 11.54 | 0.02 |
| 5 | 13.19 | 0.00 |
| 6 | 11.54 | 0.30 |
| 7 | 0.00 | 0.04 |
| 8 | 0.00 | 0.00 |

Sample Position
- ● 1   ○ 5
- ○ 2   ○ 6
- ○ 3   ○ 7
- ○ 4   ○ 8

Present Position: 4
Mout Position: [ ]

SET FLOWS
STOP FLOWS
PURGE 1-4
PURGE 5-8
PURGE OFF

Sent to Fieldpoint: Source
Response from Fieldpoint: AFF84F8
Error String: [ ]

Gentle Start ●   Normal Start ○

Continue After Error

Exit Program   Help   Acquire Data

Fig. 10

Crate 3 Spectrometer Monitor

Sample Currently Under Analysis

| | |
|---|---|
| Submitter Name: | Bob Manto |
| Study Name: | 11070033 |
| Sample Name: | MT2 |
| Sample Description: | Empty Tube |
| MasterState, Cycle Number and Sample Position: | 1 1 2 |

Preset Delay (Hours): 0.03
Run Time Delay (Hours): 0.030

Delay 1 in Seconds: 11.986
Delay 2 in Seconds: 9.313
Time (Mh.): 3.25

Abort Sequence

Continue After Error

Sent to Specromoter:
SAVE/FILE=E:\DATA\RBPRAM\11070033\SPEC_2SPC

For Sample tube 1 And Sample Name :Blank

| Analysed Species | Mole % |
|---|---|
| Propane | 0.00 |
| Carbon Monoxide | 0.00 |
| Carbon Dioxide | 0.01 |
| Acrylic Acid | 0.01 |
| Acetic Acid | 0.01 |
| Carbon Account | 2 |

Returned From Spectrometer:
SAMPLE SCAN COMPLETED

Finish Sequence and Stop | Help | Begin Experiment !

METHODS AND SYSTEMS FOR HIGH THROUGHPUT ANALYSIS

CROSS REFERENCE TO RELATED PATENT APPLICATION

This is a non-provisional application of prior pending U.S. provisional application Ser. No. 60/339,903 filed on Dec. 17, 2001.

BACKGROUND OF THE INVENTION

The present invention relates generally to the field of chemical evaluation systems, and more particularly, to systems for the high throughput analysis of chemical reactions and associated chemical properties.

In the search for chemical compounds and for more efficient chemical reactions, automated systems for experimentally testing chemical reactions have been developed. Typically, these systems subject a known chemical composition or set of chemical compositions to a predefined set of reaction variables. If the test reaction or the output of the reaction exhibits desirable properties, further investigation of the particular reaction or composition may be warranted.

Automated testing is frequently used in the area of catalyst development. Generally, catalyst screening systems involve confining a compound in a pressure vessel and contacting the compound with one or more fluid phase reactants at a controlled temperature, pressure, and flow rate. If the compound produces some minimal level of reactant conversion to a desired product, the compound undergoes more thorough characterization in later processes.

One such automated system for screening catalysts is disclosed in U.S. Letters Patent No. 6,149,882. This document discloses a system for screening members of a combinatorial library by contacting library members with a test fluid. The system comprises a single volume of reactant fluid which is simultaneously applied to a combinatorial library of chemical compositions. The system is especially designed so that all members of the combinatorial library experience an identical fluid flow, under identical pressures and temperature. The system is said to provide the benefit of increasing the speed at which combinatorial libraries of chemical compositions can be screened for catalytic characteristics. In addition, this document discloses the use of multiple reactors and a sampling probe positioned to sample the vessel effluent.

There are, however, numerous unsatisfied needs in the art. In particular there is a need for automated systems and methods for simultaneously analyzing chemical compositions under independent sets of reaction conditions. For example, there is a need for a system wherein a plurality of disparate chemical compositions can be simultaneously analyzed using different flow rates, under different pressures and temperatures. Such a system would provide much needed speed and flexibility in the analysis of chemical compounds, including catalyst analysis.

The present invention meets these and other needs in the art. Generally, the invention is directed to a high throughput analysis system that provides the capability to define and execute in rapid succession a plurality of experiments under disparate reaction conditions. An operator may define and execute a plurality of experiments on user-defined quantities of disparate chemical compositions, using user-defined input feeds, residence times, and temperature profiles.

STATEMENT OF INVENTION

In a first aspect of the present invention there is provided a method of analyzing any one or more of the following: at least one physical property of a reaction product, at least one chemical property of a reaction product, at least one performance property of composition used in producing a reaction product, at least one of the effects of any one or more reaction conditions on a reaction product, and at least one of the effects of any one or more reaction conditions on at least one performance property of any composition used in producing a reaction product, wherein said method comprises at least the following:

a. providing at least a first and a second reaction zone, wherein said first and said second reaction zones each have associated therewith a plurality of corresponding reaction conditions, and wherein at least one of the reaction conditions associated with the first reaction zone is capable of being modified independently of the corresponding reaction condition associated with the second reaction zone;

b. providing in said first reaction zone at least a first catalyst and a first reactant;

c. providing in said second reaction zone at least a second catalyst and a second reactant, said first catalyst can be the same or different from said second catalyst, and said first reactant can be the same or different from said second reactant;

d. subjecting at least one of said reaction zones to a set of reaction conditions to produce a reaction product; and e. analyzing said reaction product to determine at least one of the following: at least one physical property of said reaction product, at least one chemical property of said reaction product, at least one performance property of said first catalyst, at least one performance property of said second catalyst, at least one performance property of said first reactant, at least one performance property of said second reactant, at least one of the effects of any one or more reaction conditions a physical or chemical property of the reaction product; at least one of the effects of any one or more reaction conditions a performance property of the first or second catalysts, and at least one of the effects of any one or more reaction conditions on a performance property of the first or second reactants.

In a second aspect of the invention there is provided a system for analyzing any one or more of the following: at least one physical property of a reaction product, at least one chemical property of a reaction product, at least one performance property of a reactant used in producing a reaction product, at least one of the effects of any one or more reaction conditions on a reaction product, and at least one of the effects of any one or more reaction conditions on at least one performance property of any reactant used in producing a reaction product, wherein said system comprises at least the following:

a. at least a first and a second reaction zone, each having associated therewith an inlet through which at least one reactant is introduced and an outlet through which at least one reaction product produced therein is expelled, b. a first controlling system for controlling at least one of the following reaction conditions for the first reaction zone: its temperature profile, the rate at which at least one reactant is introduced therein through its inlet, and the rate at which at least one reaction product is expelled therefrom through its outlet, and a second controlling system for controlling at least one of the following reaction conditions for the second reaction zone: its temperature profile, the rate at which at least one reactant is introduced therein through its inlet, and the rate at which at least one reaction product is expelled therefrom through its outlet, wherein at least one of said reaction conditions associated with the first reaction zone is capable of being controlled independently of the corresponding reaction condition associated with the second reaction zone; and c. an analyzing system for analyzing at least one reaction product expelled from the first or second reaction zones to determine at least one of the following: at least one physical property of said reaction product, at least one chemical property of said reaction product, at least one performance property of a reactant used in producing a reaction product, at least one of the effects of any one or more reaction conditions on a reaction product, and at least one of the effects of any one or more reaction conditions on at least one performance property of any reactant used in producing a reaction product.

In a third aspect of the present invention, there is provided a method for controlling the analysis of catalysts, comprising at least the following:

a. receiving reaction input data defining a plurality of chemical reactions to be performed under distinct reaction conditions in a plurality of reaction zones;

b. communicating with a heating element and at least one of a plurality of input controls to create the plurality of chemical reactions defined by the reaction input data in the plurality of reaction zones;

c. communicating with at least one valve to control an output flow out of one of the plurality of reaction zones; and d. communicating with a detector to analyze the output flow out of one of the plurality of reaction zones.

BRIEF DESCRIPTION OF THE DRAWINGS

Other features of the invention will be further apparent to those of ordinary skill in the art from the following detailed description of certain specific embodiments of the invention taken in conjunction with the accompanying drawings, of which:

FIG. 7 depicts an exemplary user interface screen for the input of data relating to test sample reaction conditions in accordance with an aspect of the invention;

FIG. 8 depicts an exemplary user interface screen for the input of operator temperature settings in accordance with an aspect of the invention;

FIG. 9 depicts an exemplary user interface screen for the input of data related to flow rate control in accordance with an aspect of the invention;

FIG. 10 depicts an exemplary user interface screen related to test sample analysis data in accordance with an aspect of the invention;

DETAILED DESCRIPTION OF THE INVENTION

Figure 1:
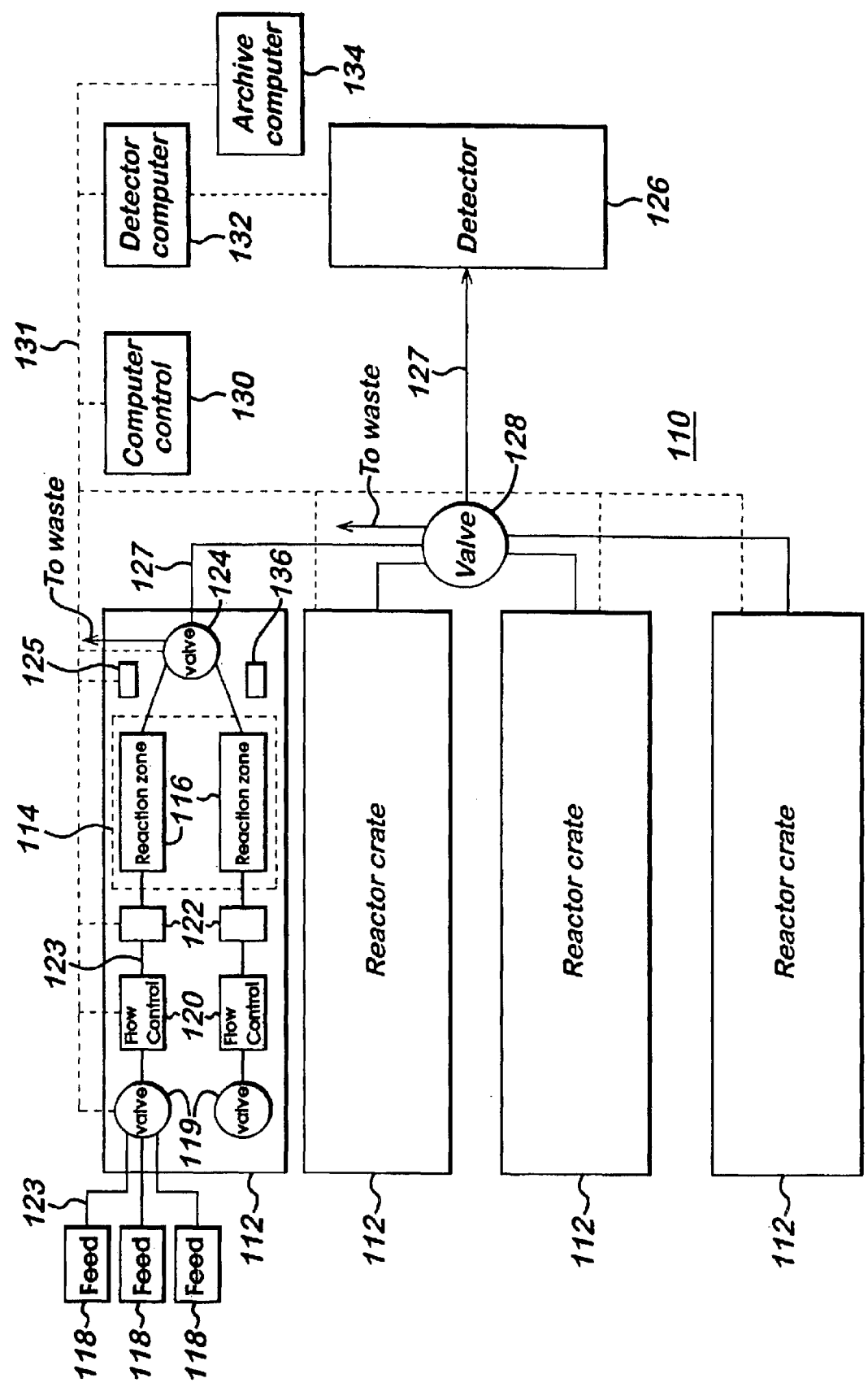
FIG. 1 is a schematic diagram of an exemplary embodiment of an analysis system in accordance with the present invention.

FIG. 1 is a schematic diagram of an exemplary embodiment of an analysis system 110 in accordance with the invention. System 110 comprises a plurality of reaction blocks 112 that house a reactor core 114. Reactor core 114 houses one or more reaction zones 116 that receive sample catalysts that are the subject of analysis.

Each reaction zone 116 comprises an inlet through which at least one reactant is introduced and an outlet through which at least one reaction product produced therein is expelled. Each reaction zone 116 is in fluid communication with various input controls that include, for example, one or more reactant feed sources 118 and associated valving 119, mass flow controllers 120, and/or moisture saturators 122. As shown in FIG. 1, the components of the analysis system are connected via feed lines 123 and other associated piping.

Reaction product produced within reaction zones 116 flows to reaction zone selector valve 124 which is operable to selectively route the reaction product. Generally, reaction zone selector valve 124 routes the reaction product from one reaction zone 116 on to reaction core selector valve 128, while routing the output flow from the remaining reaction zones 116 to waste. In embodiments comprising multiple reaction blocks 112 and reactor cores 114 as shown in FIG. 1, the system comprises a reactor core selector valve 128 that receives designated reaction product streams from each reactor core 114 and is capable of selectively routing the reaction products to a waste stream or to the detector 126 for analysis. Output flow line heating element 125 operates to heat reaction product flow lines 127 to prevent exhaust gases from condensing in lines 127. Reactor core heating element operates to heat reactor core 114 to the desired experimental temperature.

Analysis system 110 further comprises one or more control computers 130 that communicate with other components of the system to independently control the reaction conditions of each reaction zone 116 and selectively analyze the reaction products produced therein. As shown in FIG. 1, control computer 130 communicates with other system components over communication bus 131. In embodiments having more than one reactor block 112, each reactor block 112 may be associated with a separate control computer 130. Alternatively, a single control computer 130 may control each of a plurality of reactor blocks 114. Examples of reaction conditions controlled by control computer 130 include, for example, the temperature profile of reaction zones 116, the rate at which at least one reactant is introduced to reaction zones 116, and the rate at which at least one reaction product is expelled from reaction zones 116. Control computer 130 also communicates with detector computer 132 to implement analysis requests. Furthermore, control computer 130 communicates with data archive computer 134 to maintain an archive of the analysis parameters and results.

Figure 2:
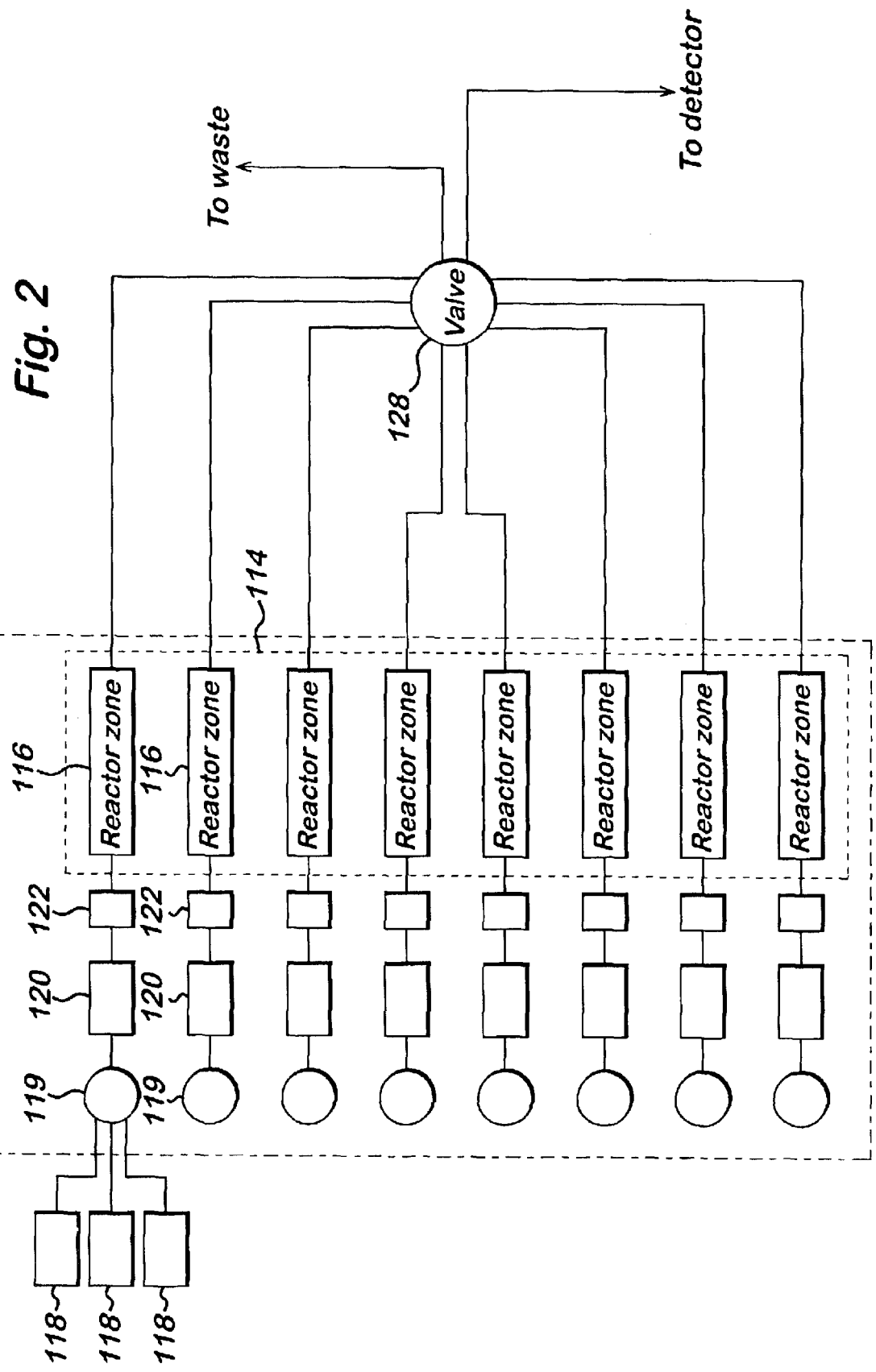
FIG. 2 is a schematic diagram of a reactor block in accordance with an aspect of the present invention.

FIG. 2 is a schematic representation of a single reactor block 112. Reactor block 112 comprises a plurality of reaction zones 116, each of which may house a catalyst to be analyzed. Although the present invention may be discussed in terms of catalyst analysis, the catalyst may be any composition, liquid or solid, sought to be analyzed. These other uses will become evident to those skilled in the art after reading this specification.

Typically, a solid chemical composition (e.g., a catalyst) is supplied to reaction zones 116 in the form of a fixed bed. The catalyst may be supported on solid particles or may itself be granular or a porous solid. Reaction zones 116 preferably comprise a reaction tube of specified dimensions that is capable of supporting a catalyst bed. Generally, the reaction zone may be any vessel or container capable of supporting a catalyst. Depending on the property or reaction condition being analyzed, each catalyst may be loaded into a different reaction zone 116 in the same or different amounts, at the same or different heights, and with the same or different particle sizes.

In accordance with the specific embodiment of the invention illustrated in FIG. 1, one or more reactants is introduced to one or more reaction zones 116. Each reaction zone 116 is in fluid communication with one or more input controls such as a reactant feed source 118. In the exemplary embodiment, an individual reaction zone 116 may be in fluid communication with one or more reactant feed sources 118. A selector valve 119 is used to select one or more reactants. In alternative embodiments, one reactant feed source 118 may be used to supply a reactant to each reaction zone 116 within an individual reactor core 114. In addition, a different reactant feed source 118 may be associated with each individual reactor core 114. The reactants may be liquids or gases and may include, for example, hydrocarbons compositions, such as those containing at least one of the following: methane, ethane, propane, butane, propylene, etc.

Another input control in fluid communication with reaction zone 116 includes one or more mass flow controllers 120. As depicted in FIG. 2, a mass flow controller 120 controls the flow rate of each reactant introduced into an individual reaction zone 116. Accordingly, residence time may be varied from reaction zone to reaction zone by changing the flow rate of a reactant being introduced. For example, depending on the dimensions of the reaction zone, catalyst particle size, and catalyst bed height, flow rate may be varied over a range of rates that will correspond to a range of residence time. Residence time for this specific embodiment is defined as The time the reactant(s) is in contact with the catalyst(s) under a specific set of reaction conditions. In addition, control of the rate of flow rate into a reaction zone 116 also serves to control the rate at which a reaction product is expelled from a reaction zone 116.

Optionally, one or more reaction zones 116 may be in fluid communication with a moisture controller such as a moisture saturator 122. In this specific embodiment, moisture saturator 122 can provide and/or regulate the moisture content of the reactant(s) and/or the reaction zones 116.

In the system illustrated in FIG. 1, each reaction zone 116 is housed in reactor core 114. Specifically, in this exemplary embodiment, eight reactor zones 116 are housed in a single reactor core 114. Of course, more or less reactor zones 116 may be associated with a single reactor core 114.

In one specific embodiment, the temperature of each reaction zone 116 can be controlled at the reactor core 114 level. Under such circumstances, each reactor core 114 can be in thermal communication with a heating element. With this specific configuration, the temperature of each reactor core 114 and its associated reaction zones 116 can be regulated by, for example, control computer 130.

Reaction zones 116 typically have the same temperature profile as their corresponding reactor core 114. Reactor core temperature profiles are typically defined by their temperature ranges, their ramp rates and/or their dwell times. These parameters can be regulated by any suitable means. In the specific embodiment illustrated in FIG. 1, they are regulated by control computer 130.

Reactor core temperatures, ramp rates and dwell times for a specific system made in accordance with the present invention depend, in part, upon the product being made, the property being analyzed, and/or the materials from which the system's components are manufactured. When practicing this embodiment of the invention, those skilled in the art, after reading this disclosure, will be able to determine the core temperatures, ramp rates and dwell times that best suits their needs. All such configurations are deemed to be encompassed by the present invention. In addition to altering temperature profiles on a run by run basis, in embodiments comprising multiple reactor cores, it is also within the scope of this invention for the temperature profile of individual reaction zones to be simultaneously varied.

As one example, if the system illustrated in FIG. 1 is designed for the catalytic conversion of hydrocarbons (e.g., propane and/or propylene—containing reactants) to unsaturated aldehydes or acids, the reactor core temperature will typically range from 150° C. to 1000° C., and more typically from 250° C. to 750° C. Moreover, the ramp rate will typically range from 0.10° C./min to 25° C./min, and more typically from 1° C./min to 10° C./min.

Figure 3:
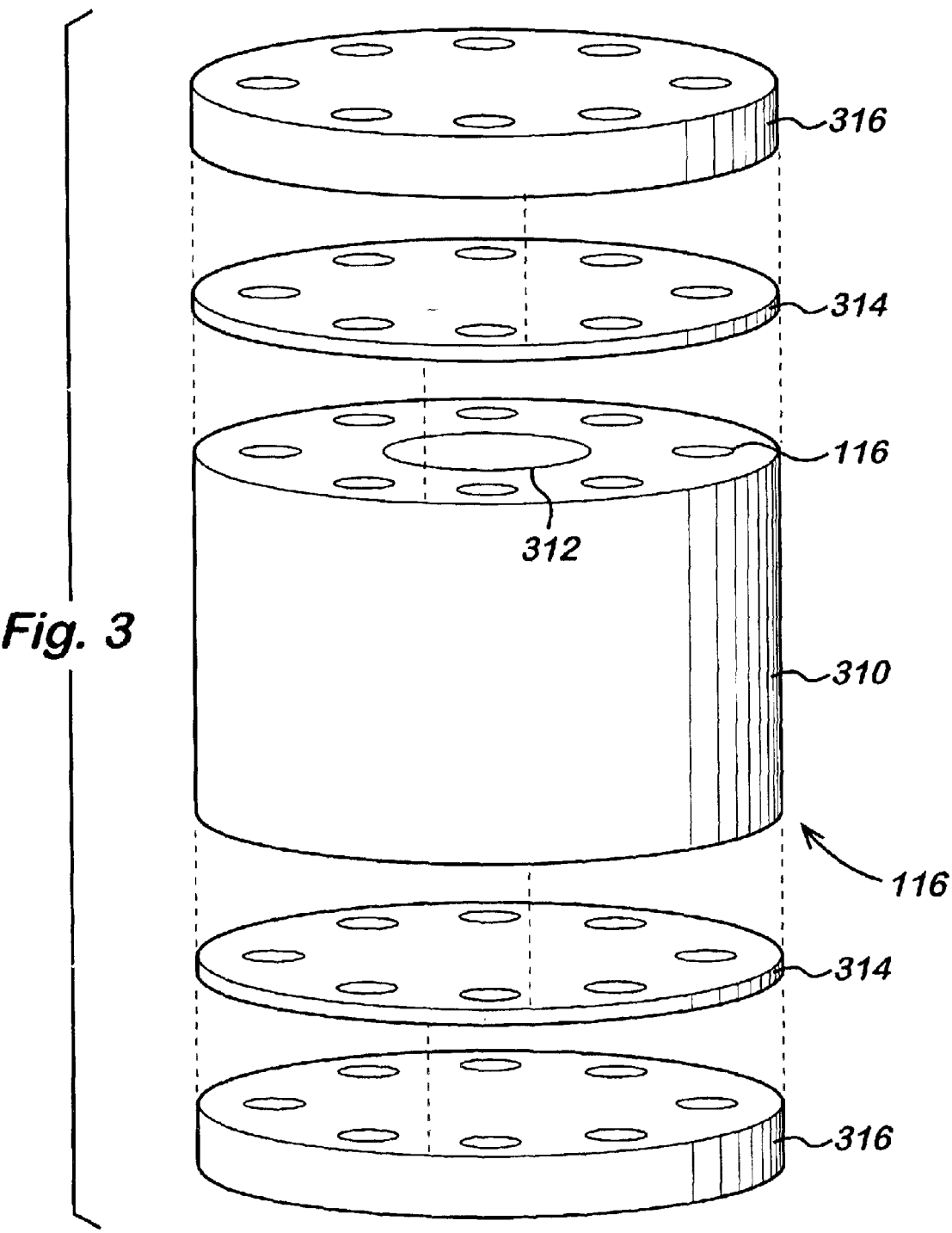
FIG. 3 is an exploded view of a reactor core in accordance with an aspect of the present invention.
Figure 4:
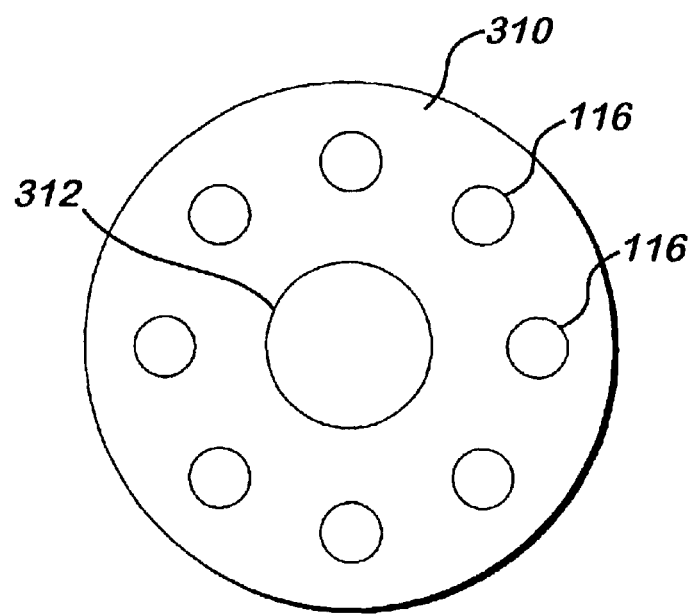
FIG. 4 is top view of a reactor core in accordance with an aspect of the present invention.
Figure 5:
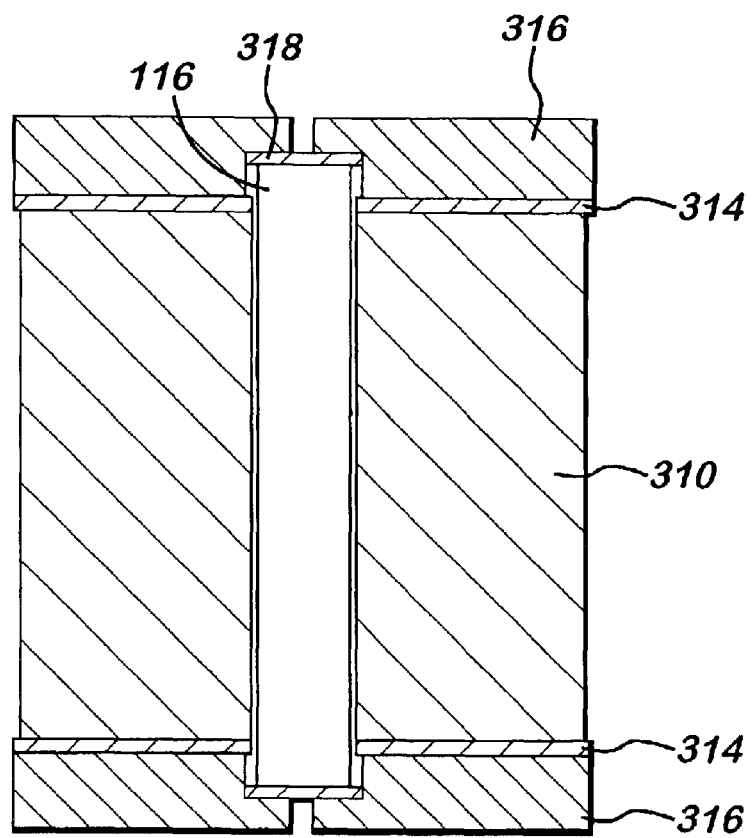
FIG. 5 is a sectional view of a reactor core in accordance with an aspect of the present invention.

The design of reactor core 114 aids the overall throughput of the system. An exemplary embodiment of reactor core 114 is depicted in FIGS. 3–5. As shown, reactor core 114 comprises a cylindrical block 310 having a hollow center 312.

Block 310 can be made of any suitable material that can withstand the particular temperature profile and/or reaction conditions to which it is to be subjected. In the specific embodiment illustrated in FIG. 1, block 310 can be made out of a material such as, for example stainless steel.

Reaction zones 116 are distributed symmetrically around block 310 at a uniform radius from the center of the cylinder. All configurations of reaction zones within block 310 are, however, encompassed by the present invention. If it is desired for reactor block 310 not to be affected by the addition of small masses associated with the reactants in reaction zones 116, reactor block 310 will typically have a relatively large thermal mass.

When used to make unsaturated aldehydes or acids from lower chain hydrocarbon compositions, temperatures within reactor block 310 typically can reach as high as 1000° C. At these temperatures, it is often desirable to uses insulators 314 positioned on opposite ends of reactor block 310 to isolate other system components from the intense heat. Insulator 314 may be manufactured from any suitable material that can provide sufficient insulation. In this specific embodiment, insulator 314 can be manufactured, for example, out of ceramic composite material.

In the system illustrated in FIG. 1, input manifolds 316 are positioned adjacent insulators 314 and serve to further thermally isolate reactor block 310. Generally, a cooling fluid can be circulated in input manifolds 316, if desired. Input manifolds are manufactured from any suitable material. In this specific embodiment, input manifolds can be manufactured from stainless steel.

Reactor core 114 also comprises sealing rings 318. If used, sealing rings 318 operate to provide a tight seal around the inlets of the reaction zones without having to exert large amounts of pressure. This is especially useful when the reaction zones are made from a more fragile material such as glass or quartz, as opposed to a more rigid material such as stainless steel. However, it is within the scope of this invention to use sealing rings with the more rigid reaction zones such as those made out of steel.

Referring back to FIG. 2, detector 126 is operable to analyze the reaction product expelled from the reaction zones 116 to determine at least one of the following: at least one physical property of said reaction product, at least one chemical property of said reaction product, at least one performance property of a reactant or catalyst used in producing a reaction product, at least one of the effects of any one or more reaction conditions on a reaction product, and at least one of the effects of any one or more reaction conditions on at least one performance property of any reactant or catalyst used in producing a reaction product.

Depending on the analytical device being employed, the high throughput system disclosed herein can be used to analyze any number or physical, chemical or performance properties of reactants, catalysts or reaction products. The specific properties being analyzed will depend upon the specific goals and objectives of the end user.

In the embodiment wherein the system is used to make unsaturated aldehydes or acids, an example of physical, chemical and performance properties that can be analyzed are as follows. Examples of physical properties that can be analyzed included thermal conductivity, adsorption, porosity, viscosity, specific gravity, heat capacity, dielectric constant, and the like. Examples of chemical properties include spectroscopic properties, compositional data, pH, molecular mass, molecular structure, and the like. Examples of performance properties of the reactant or catalyst include reactivity, conversion, percent yield, absorption, stability, selectivity, and the like.

Detector 126 can be any suitable device. The specific type of device employed when practicing an embodiment of this invention will depend, in part, on the properties being analyzed. However, in the specific embodiment wherein the system is being used to make unsaturated aldehydes or acids, detector 126 is typically a spectroscopic or chromatographic device. In certain preferred embodiments, it is envisioned that an infrared spectrometer is used to generate an infrared spectrum of the reaction product; and Partial Least Squares (PLS) is used to mathematically separate and analyze individual analyze concentrations. Detector 126 may also be designed to provide low dead volume that requires short purge times to further aid in maintaining a high throughput for the system.

Although the system depicted in FIG. 1 shows a single detector 126, it is within the scope of this invention that a number of detectors can be used. In addition, detector 126 may also comprise multiple channels to further expedite the analysis process.

Figure 6:
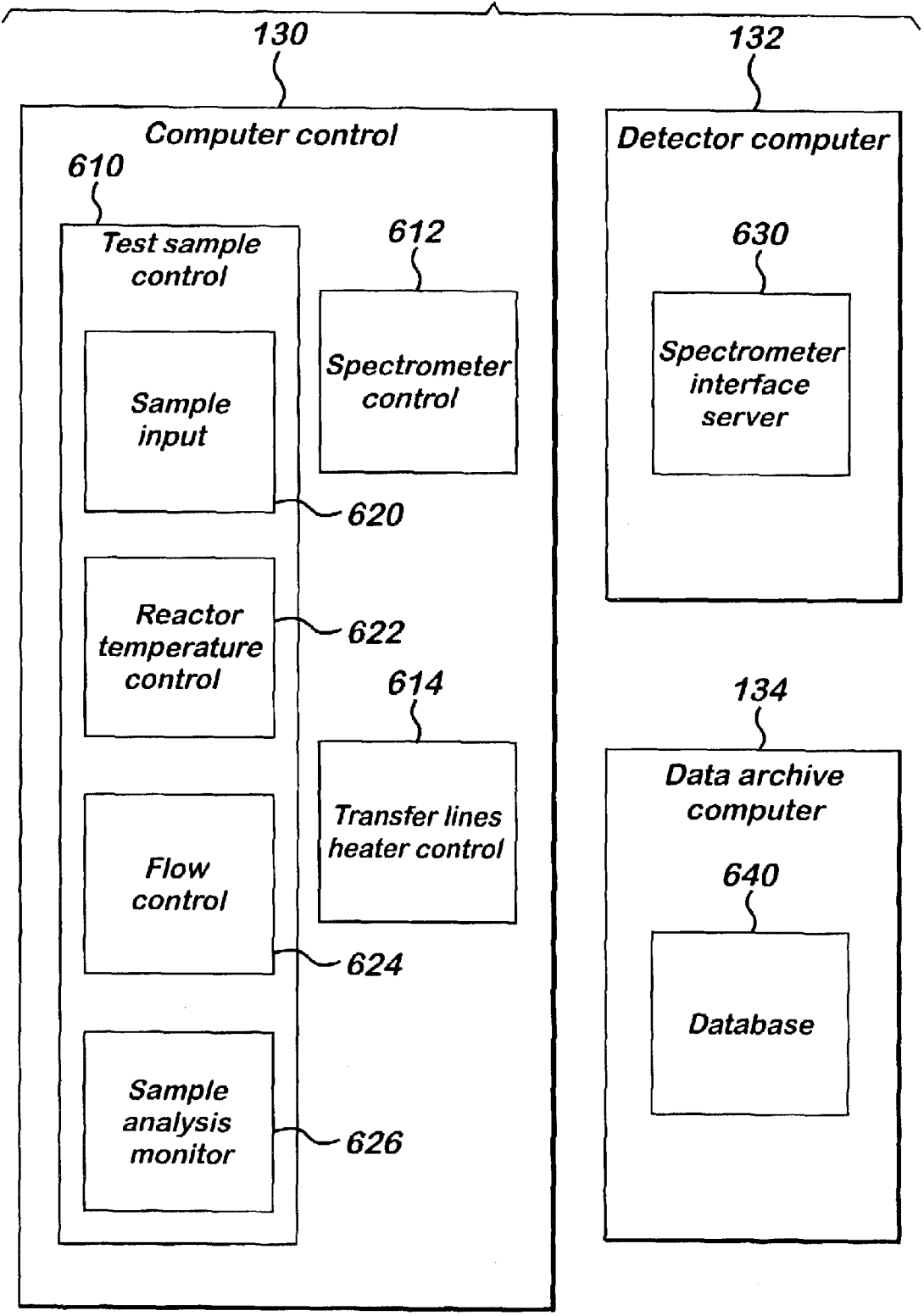
FIG. 6 is a block diagram of software components comprised in an exemplary embodiment of a system in accordance with the invention.

FIG. 6 is a block diagram of software components that may be employed in the exemplary embodiment of a system in accordance with the invention. As shown, the specific control computer 130 comprises the following software components: test sample control 610, spectrometer control 612; and transfer lines temperature control 614.

It should be noted that, after reading this disclosure, those skilled in the art will learn how to make modifications to the block diagram. Such modifications are deemed to fall within the scope of this invention. For example, spectrometer control 612 can be any control for any analytical device. Similarly, transfer lines heater control 614 can be a moisture control, or the like. Set out below is a description of a fairly specific block diagram of software components encompassed by this invention.

In this specific embodiment, test sample control module 610 provides a user interface and also communicates with reactor cores 114 and selector valves 124 and 128 of the system illustrated in FIG. 1 to implement a plurality of reactions specified by the operator. In the exemplary embodiment, a single instance of sample control module 610 is responsible for the experiments implemented at a single reactor core. For each reactor core 114 that is used, a unique instance of test sample control module 610 is substantiated. Thus, while only a single instance of test sample control 610 is shown in FIG. 6, multiple instances may be operating on control computer 130. Furthermore, each instance of test sample control 610 may operate on a separate computing device.

In the specific block diagram illustrated in FIG. 6, test sample control module 610 comprises test sample input module 620, reactor temperature control module 622, flow control module 624, and sample analysis monitor module 626. Test sample input module 620 provides for defining new test sample experiments. Specifically, test sample input module 620 allows the operator to define the reaction conditions for a plurality of test sample experiments.

After reading this disclosure, those skilled in the art would be able to configure data on a computer screen in an infinite number of ways depending upon their specific needs and objectives. One example of a user interface screen that can be associated with input module 620 for defining test sample reaction conditions is illustrated in FIG. 7. As shown therein, establishing a new test protocol involves identifying a sample, the sample's mass, the sample's height, and a residence time. For example, a user may define that sample X, having a mass of 2 grams and a height of 4 cm, is to undergo testing with a residence time of 5 seconds. The residence time is defined as the sample volume divided by the flow rate. In certain preferred embodiments, the sample volume is the cylindrical volume in the catalyst tube, which in the exemplary embodiment is equal to the sample height multiplied by $\Pi r^2$, where r represents the radius of the catalyst tube. Using values for the residence time and the sample volume, a flow rate for the test sample is calculated.

The exemplary user interface of FIG. 7 also provides for identifying the name of the party submitting the sample, a description of the sample, and the contents of the sample. Although not shown in the exemplary screen, a system in accordance with the invention further provides the capability to specify the input feed that is to be used. For example, an operator of the system may specify that the input fluid is to be hydrogen as opposed to some other feed source gas.

Thus, a system in accordance with this embodiment of the invention provides for entering a plurality of test samples, each of which may have different masses, heights, and residence times. Further, each test sample experiment may be specified to be conducted with a particular reactant feed source. Collecting this information, which defines the reaction conditions for a plurality of chemical reactions, allows for defining a plurality of unique experiments which can be run simultaneously. By comparison, existing systems operate to expose test samples, which have a common size and configuration, to a common test protocol under the same flow rate. Accordingly, a system in accordance with this embodiment of the present invention provides versatility that is not provided by existing systems.

Test sample control module 610 of the specific block diagram illustrated in FIG. 6 further comprises reactor temperature control module 622. Generally, reactor core temperature control module 622 allows for the operator of the system to specify temperature conditions for reactor core 114. This can also be used to specify temperature conditions of defined sections of the reactor core such that the temperature conditions of the defined sections can be controlled independently. These temperature conditions are implemented in reactor core 114, or one or more defined sections, while the test sample experiments, which have been specified as explained above in connection with FIG. 7, are executed.

One specific example of a screen that can be implemented by reactor temperature control module 622 for gathering operator temperature settings is illustrated in FIG. 8. After reading this disclosure, those skilled in the art would be able to configure this data on an interface screen in an infinite number of ways depending on their needs and objectives.

As shown in the specific screen illustrated in FIG. 8, the operator can specify an initial temperature value and a period for which the initial temperature is to be held. Thereafter, the temperature may be increased by an operator defined gradient until reaching an operator defined plateau value. In this specific example, the operator can specify up to five such "ramps" which are executed sequentially. Once a set of temperature ramp settings have been defined, they may be saved and recalled for use in future tests.

Test sample control module 610 of the specific block diagram illustrated in FIG. 6 further comprises flow control module 624. Flow control module 624 can provide an interface for displaying the present flow data as well as allowing the user to change those flows.

One specific example of a user interface screen which can correspond with flow control module 624 is illustrated in FIG. 9. As shown, for each of the eight reaction zones 116 that are comprised in reactor core 114 of the exemplary test system, the actual flow rate and the desired flow rate are displayed. Values for the desired flow rates are calculated based upon the residence time defined by the operator as explained above in connection with FIG. 7. The operator can change the flow rate from that calculated by the system simply by introducing a new value in the appropriate location.

Flow control module 624 can also be configured to control the queuing of tests within a reactor core 114 for analysis. Thus, flow control module 624 can be used to determine which experiment is to be implemented within a particular reactor core 114.

In one specific example, flow control module 624 queues test samples within a reactor core on a first-in-first-out basis. When a test sample is next in the queue, the flow control module can be configured to communicate with the various components of the test apparatus including feed source selector valves 119, mass flow controls 120, and saturators 122 to implement the flow settings associated with the particular test sequence. Thus, flow control module 624 can identify which test is to be analyzed and activate the various components of the apparatus to insure that the reaction conditions correspond to those specified by the operator. Once the reaction conditions have been established, flow control module 624 can be designed to communicate with reaction zone selector valve 124 to direct the output flow from the queued test reaction to reactor core selector valve 128.

Test sample control module 610 of the specific block diagram illustrated in FIG. 6 further comprises sample analysis monitor module 626. Sample analysis monitor module 626 can be configured to provide an interface to the test screening that is presently being analyzed at detector 126.

One specific example of a user interface screen which can correspond to sample analysis monitor module 626 is illustrated in FIG. 10. As shown, the test sample experiment presently being analyzed is identified along with the physical readings for that test sample.

Referring back to the specific block diagram illustrated in FIG. 6, control computer 130 further comprises spectrometer control module 612. Spectrometer control module 612 can be used to determine which test sample, from amongst those queued at each of the reaction cores 114, is to be analyzed next. Spectrometer control module 612 can also be used to communicate with reactor core selector valve 124 to route the flow from the appropriate reactor core 114 to detector 126, and to communicate with detector computer 132 as to when to begin operating on the reaction product flow stream.

As explained above, for the plurality of reaction zones 116 associated with any one particular reactor core 114, flow control module 624 is responsible for identifying which of the reactions is to be implemented at any particular time. Accordingly, flow control module 624 controls the operation of reaction zone valves 124 and thereby identifies which test sample within a reaction core 114 is to be analyzed.

Spectrometer control module 612 can be configured to control reactor core selector valve 128 and thereby identify which test sample across the reactor cores is to be analyzed. Generally, in this specific embodiment, spectrometer control module 612 operates on a modified first-in-first-out algorithm. The basic rule of operation is typically that the test sample that has been waiting the longest across the reactor cores 114 is selected for evaluation next. However, if there is a long purge delay associated with that particular test sample, and another one of the queued experiments can be performed before the delay elapses, the other test experiment may be implemented first.

Another embodiment of this invention pertains to an algorithm for queuing test sample experiments. One example of a flow diagram of such an algorithm is illustrated in FIG. 11.

Figure 11:
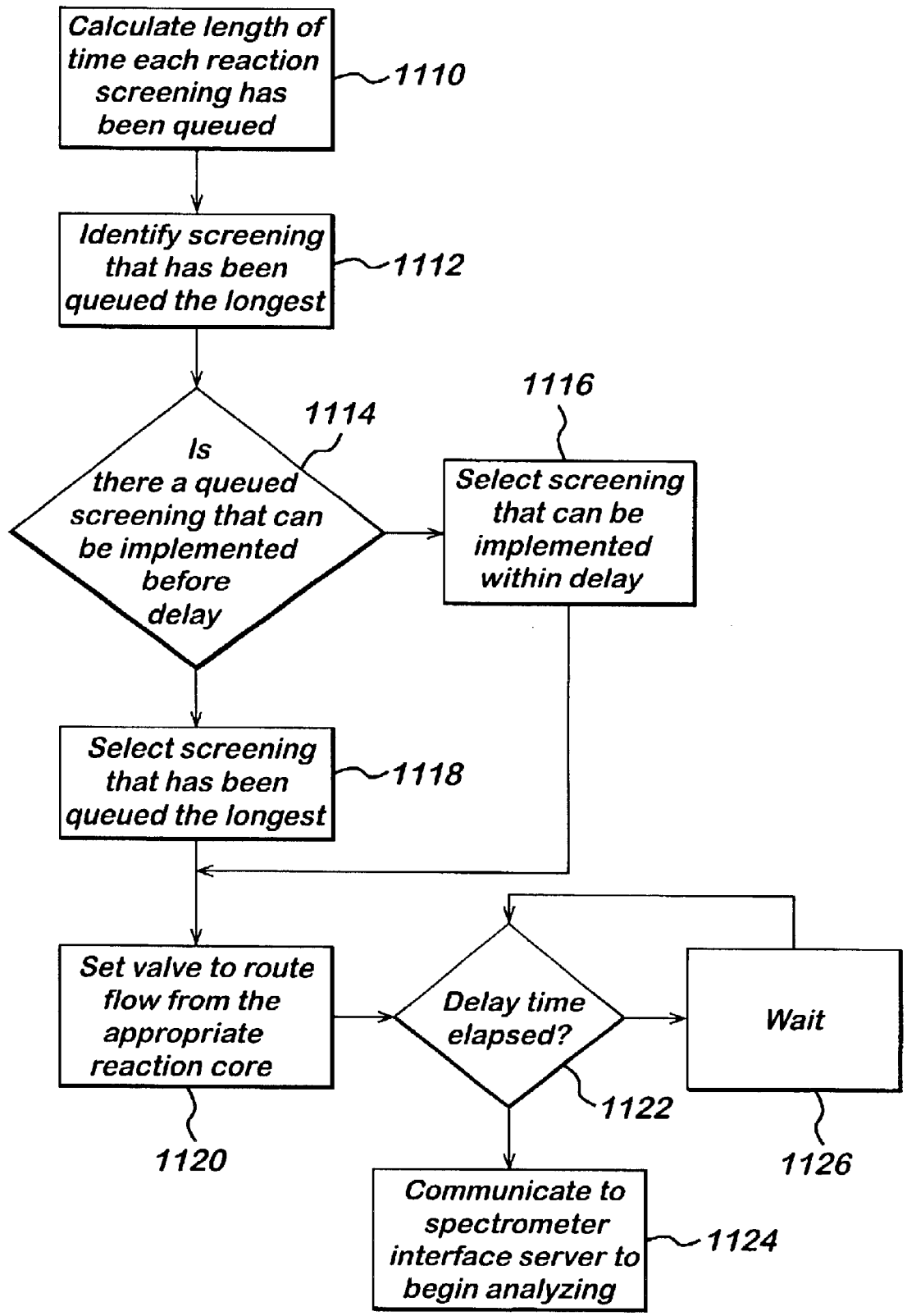
FIG. 11 depicts a flow diagram of the algorithm for queuing test sample experiments in accordance with an aspect of the invention.

As shown, at step 1110 of the flow diagram illustrated in FIG. 11, spectrometer control module 612 calculates the length of time that each test sample has been waiting to be analyzed. At step 1112, the sample that has been queued the longest is determined. At step 1114, module 612 determines whether any of the test samples that are waiting to be analyzed can be implemented in less time than the delay associated with the test sample that has been queued the longest. If so, that sample is selected as the next test sample to be analyzed at step 1116. If there is not another test sample that can be analyzed within the delay time associated with the test sample that has been queued the longest, the test sample that has been queued the longest is selected for testing at step 1118. At step 1120, reactor core selector valve 128 is set to route the reaction product from the appropriate reactor core. At step 1122, spectrometer control module 612 determines if the appropriate delay time associated with purging gas feed lines 127 has elapsed. If so, at step 1124, module 612 communicates to spectrometer interface server 630 to begin implementing the queued test experiment.

Referring back to the specific block diagram illustrated in FIG. 6, control computer 130 further comprises transfer lines heater control module 614. Transfer lines heater module 614 is responsible for controlling the heating of lines 127 leading out of the reaction zones to detector 126. For certain uses, it may be desirable to maintain transfer lines 127 heated to at least a minimum temperature in order to prevent condensing of the reaction flow on its way from reaction zones 116 to detector 126. Transfer lines heater control 614 can be configured to operate with heating element to bring the transfer lines up to, and/or maintain, a desired temperature or temperature profile.

Again referring back to the specific block diagram illustrated in FIG. 6, detector computer 132 comprises spectrometer interface server 630. Spectrometer interface server 630 is responsible for receiving requests to implement spectrometer screenings from spectrometer control module 612 and communicating with detector 126 to physically implement the request. Spectrometer interface server 612 can also be configured to relay the readings from detector 126 back to spectrometer control module 612.

Referring once again to FIG. 6, data archive computer 134 comprises archive database 640. Archive database 640 is responsible for maintaining an archive of the screening tests that have been performed. Accordingly, as test samples are analyzed, the data is archived in archive database 640 for later retrieval and analysis.

As stated above, the preferred configuration of the high throughput systems and analytical methods disclosed herein depends, in part, of the desired needs and objectives of the end user. Those skilled in the art will, however, be able to design such preferred systems and methods after reading this disclosure. Some examples of certain optional/preferred embodiments of the high throughput systems and analytical methods disclosed herein are set out below.

Specifically, in certain preferred embodiments, the reaction product produced in the high throughput system is not injected into a mobile-phase detector. Instead, once the desired reaction product sample is selected, the entire amount of the sample passes directly through the detector. In this embodiment, no separate mobile phase is necessary or utilized.

In other preferred embodiments of the high throughput systems disclosed herein, a sampling probe is not used to remove and transport a reaction product sample to a detector.

In still other preferred embodiments, a selection valve is used to select a single stream of a reaction product sample to be sent to the detector. In this preferred process, a sampling valve which diverts a portion of the reaction product flow of the single stream to the detector and returns the non-diverted flow to a waste stream via a return line is not utilized. Instead, in this embodiment, the high throughput system directs the entire selected stream to the detector.

In yet other preferred embodiments, the high throughput system utilizes a valve to select the desired reaction product stream. That valve, however, does not provide selective fluid communication between an inert fluid source and flow restrictors since an inert purge fluid is not used.

EXAMPLES

Examples 1–3 demonstrate certain aspects of the flexibility of the present high throughput system. In each example, different, multiple catalyst compositions are evaluated in separate reactor block experiments under different reaction conditions.

The catalyst samples were prepared by traditional methods to obtain granules of 10 to 20 mesh fraction. The granules are loaded to PYREX® reactor tubes (i.e. reaction zones) of specified dimension: length=11.6 cm, outer diameter=6.3 mm, and wall thickness=1.2 mm. The tubes contained a glass wool plug to support the catalyst bed. The reaction zones were loaded by height with nominal catalyst bed height being 4 cm.

The analysis system consisted of three reactor cores, each containing a reactor core that has eight reaction zone positions. Position one in each reactor core was reserved for a blank tube used to obtain a background spectrum for effluent gas analysis of the remaining reaction zone samples. Accordingly, seven catalysts were analyzed in each reactor core run. Analysis of the effluent gas was by a single infrared spectrometer. Requests for analysis and rate of sampling was determined by the control computer in accordance with the present invention.

Although it may be varied, the reactant feed composition was fixed at 1.0 mol % propane in air saturated with water at ambient conditions for each reactor core experiment. Residence time was varied from sample-to-sample by changing the reactant feed gas flow rate over the range of 5 ml/min to 20 ml/min. This corresponded to a range of residence time on a normal 4 cm sample of approximately 3 to 12 seconds. For purposes of the present examples, evaluation conditions were programmed for 3 seconds residence time.

Temperature profiles were controlled at the reactor core and were defined by a designated ramp rate and dwell time. A total of 5 ramp and dwell segments could have been programmed for a given reactor core. Maximum reactor temperature was limited to 400° C. For purposes of the present examples, a ramp from 200° C. to 300° C. at 5° C./minute followed by a ramp from 300° C. to 400° C. at 1° C./minute with a 5 minute dwell between steps was performed for each sample. Each sample was analyzed at different temperatures.

In the following examples, each catalyst was prepared individually. Catalyst samples of common composition are distinguished from one another by differences such as calcination temperatures and calcination atmospheres as indicated. The samples were evaluated concurrently as grouped in three separate reactor core runs. The results tabulated include the temperature at which the sample was analyzed, the percent of propane feed converted to any other product (Conv.), the percent of propane feed converted to carbon monoxide or carbon dioxide (COx Yield), percent of propane feed converted to acrylic acids (AA Yield), the percent of converted propane that form acrylic acids (AA Select), composition of the catalyst, and the calcination temperature and atmosphere used to prepare the catalyst.

Example 1

|   | Temp (° C.) | Conv. | COx Yield | AA Yield | AA Select | Composition | Calcination Process |
|---|---|---|---|---|---|---|---|
| A | 362 | 9% | 5% | 1% | 11% | $Mo_{1.0}V_{0.3}Te_{0.23}Nb_{0.15}$ | 550° C./Nitrogen |
| B | 365 | 7% | 4% | 1% | 14% | $Mo_{1.0}V_{0.3}Te_{0.23}Nb_{0.15}$ | 575° C./Nitrogen |
| C | 392 | 25% | 21% | 0% | 0% | $Mo_{1.0}V_{0.3}Te_{0.23}Nb_{0.15}$ | 600° C./Nitrogen |
| D | 392 | 22% | 15% | 4% | 18% | $Mo_{1.0}V_{0.3}Sb_{0.25}Nb_{0.10}$ | 575° C./Nitrogen |
| E | 370 | 41% | 38% | 1% | 2% | $Mo_{1.0}V_{0.3}Sb_{0.25}Nb_{0.10}$ | 600° C./Nitrogen |

-continued

| | Temp (° C.) | Conv. | COx Yield | AA Yield | AA Select | Composition | Calcination Process |
|---|---|---|---|---|---|---|---|
| F | 395 | 39% | 37% | 0% | 0% | $Mo_{1.0}V_{0.3}Se_{0.23}Nb_{0.125}$ | 500° C./Nitrogen |
| G | 340 | 36% | 34% | 1% | 3% | $Mo_{1.0}V_{0.3}Se_{0.23}Nb_{0.125}$ | 500° C./Nitrogen |

Example 2

| | Temp (° C.) | Conv. | COx Yield | AA Yield | AA Select | Composition | Calcination process |
|---|---|---|---|---|---|---|---|
| A | 382 | 51% | 26% | 27% | 54% | $Mo_{1.0}V_{0.3}Te_{0.23}Nb_{0.125}In_{0.01}$ | 600° C./Nitrogen |
| B | 382 | 52% | 26% | 29% | 57% | $Mo_{1.0}V_{0.3}Te_{0.23}Nb_{0.125}$ | 600° C./Nitrogen |
| C | 362 | 49% | 24% | 27% | 56% | $Mo_{1.0}V_{0.3}Te_{0.23}Nb_{0.125}In_{0.005}$ | 600° C./Nitrogen |
| D | 402 | 20% | 16% | 0% | 0% | $Mo_{1.0}V_{0.3}Sb_{0.15}Ga_{0.03}Nb_{0.1}$ | 575° C./Nitrogen |
| E | 392 | 25% | 14% | 9% | 36% | $Mo_{1.0}V_{0.3}Sb_{0.15}Ga_{0.03}Nb_{0.051}$ | 600° C./Nitrogen |
| F | 369 | 62% | 43% | 17% | 27% | $Mo_{1.0}V_{0.3}Te_{0.23}Nb_{0.11}$ | 600° C./Argon |
| G | 361 | 49% | 25% | 28% | 58% | $Mo_{1.0}V_{0.3}Te_{0.23}Nb_{0.125}$ | 575° C./Nitrogen |

Example 3

| | Temp (° C.) | Conv. | COx Yield | AA Yield | AA Select | Composition | Calcination process |
|---|---|---|---|---|---|---|---|
| A | 400 | 15% | 13% | 1% | 7% | $Mo_{1.0}Sn_{0.3}Sb_{0.15}Nb_{0.05}$ | 600° C./Air |
| B | 401 | 2% | 2% | 0% | 0% | $Mo_{1.0}Sn_{0.3}Sb_{0.15}Nb_{0.05}$ | 600° C./Argon |
| C | 401 | 95% | 88% | 1% | 1% | $V_{1.0}Sb_{1.4}Sn_{0.2}Ti_{0.1}$ | 600° C./Argon |
| D | 401 | 26% | 26% | 0% | 0% | $V_{1.0}Sb_{1.4}Sn_{0.2}Ti_{0.1}$ | 600° C./Nitrogen |
| E | 401 | 49% | 45% | 1% | 2% | $Mo_{1.0}V_{0.3}Sb_{0.25}Nb_{0.15}$ | 600° C./Nitrogen |
| F | 384 | 34% | 24% | 9% | 26% | $Mo_{1.0}V_{0.3}Sb_{0.15}Nb_{0.05}$ | 575° C./Nitrogen |
| G | 401 | −1% | 0% | 0% | 0% | Empty tube (blank position) | not applicable |

The above data provides those skilled in the art with a significant amount of valuable data. Once the optimal catalyst is selected, then the system can be employed to identify the optimal reaction conditions.

Thus, the various embodiments of this invention provide methods and systems for high-throughput analysis of catalysts. According to an aspect of the invention, catalysts can be simultaneously analyzed using different reaction conditions. This provides for great flexibility and improved speed in the analysis process.

While the invention has been described and illustrated with reference to specific embodiments, those skilled in the art will recognize that modification and variations may be made without departing from the principles of the invention as described above and set forth in the following claims. Accordingly, reference should be made to the appended claims as indicating the scope of the invention.

What is claimed is:

1. A method of analyzing any one or more of the following: at least one physical property of a reaction product, at least one chemical property of a reaction product, at least one performance property of reactant or catalyst used in producing a reaction product, at least one of the effects of any one or more reaction conditions on a reaction product, and at least one of the effects of any one or more reaction conditions on at least one performance property of any reactant or catalyst used in producing a reaction product, wherein said method comprises at least the following:

a. providing at least a first and a second reaction zone, wherein said first and said second reaction zones each have associated therewith a plurality of corresponding reaction conditions, and wherein at least one of the reaction conditions associated with the first reaction zone is capable of being controlled independently of the corresponding reaction condition associated with the second reaction zone;

b. providing in said first reaction zone at least a first reactant and a first catalyst;

c. providing in said second reaction zone at least a second reactant and a second catalyst, said first reactant can be the same or different from said second reactant, and said first catalyst can be the same or different from said second catalyst;

d. subjecting at least one of said reaction zones to a set of reaction conditions to produce a reaction product; and e. analyzing said reaction product to determine at least one of the following: at least one physical property of said reaction product, at least one chemical property of said reaction product, at least one performance property of said first reactant, at least one performance property of said second reactant, at least one performance property of said first catalyst, at least one performance property of said second catalyst, at least one of the effects of any one or more reaction conditions a physical or chemical property of the reaction product; at least one of the effects of any one or more reaction conditions a performance property of the first or second reactant, and at least one of the effects of any one or more reaction conditions on a performance property of the first or second catalyst.

2. The method of claim 1, wherein at least said first catalyst comprises a catalyst.

3. The method of claim 1, wherein at least said first reactant comprises a gaseous component.

4. The method of claim 3, wherein at least said first reactant comprises a hydrocarbon.

5. The method of claim 1, wherein said reaction conditions, to which said first and said second reaction zones are subjected, each comprise at least one of the reaction conditions selected from the group consisting of: the rate at which said first or said second reactant is introduced into said first or said second reaction zones, respectively; the temperature profile of said first or said second reaction zones; and the length of time said first or said second reactant remains within the first or said second reaction zones, respectively.

6. The method of claim 5, wherein at least one of the reaction conditions to which said first reaction zone is subjected is different from the corresponding reaction condition to which said second reaction zone is subjected.

7. The method of claim 1, wherein at least one of the following conditions is present:
   a. said first catalyst is different from said second catalyst;
   b. said first catalyst is the same as said second catalyst;
   c. said first reactant is different from said second reactant;
   d. said first reactant is the same as said second reactant;
   e. said first catalyst is different from said second catalyst, and said first reactant is different from said second reactant;
   f. said first catalyst is the same as said second catalyst, and said first reactant is the same as said second reactant;
   g. said first catalyst is different from said second catalyst, and said first reactant is the same as said second reactant; and
   h. said first catalyst is the same as said second catalyst, and said first reactant is different from said second reactant.

8. The method of claim 7, wherein said reaction conditions, to which said first and said second reaction zones are subjected, each comprise at least one of the reaction conditions selected from the group consisting of: the rate at which said first or said second reactant is introduced into said first or said second reaction zones, respectively; the temperature profile of said first or said second reaction zones; and the length of time said first or said second reactant remains within the first or said second reaction zones, respectively.

9. The method of claim 8, wherein at least one of the reaction conditions to which said first reaction zone is subjected is different from the corresponding reaction condition to which said second reaction zone is subjected.

10. The method of claim 1, wherein at least one device is used to analyze said reaction product which is selected from the group consisting of: spectroscopic detection devices, and chromatographic detection devices.

11. A system for analyzing any one or more of the following: at least one physical property of a reaction product, at least one chemical property of a reaction product, at least one performance property of a reactant used in producing a reaction product, at least one of the effects of any one or more reaction conditions on a reaction product, and at least one of the effects of any one or more reaction conditions on at least one performance property of any reactant used in producing a reaction product, wherein said system comprises at least the following:
   a. at least a first and a second reaction zone, each having associated therewith an inlet through which at least one reactant is introduced and an outlet through which at least one reaction product produced therein is expelled,
   b. a first controlling system for controlling at least one of the following reaction conditions for the first reaction zone: its temperature profile, the rate at which at least one reactant is introduced therein through its inlet, and the rate at which at least one reaction product is expelled therefrom through its outlet, and a second controlling system for controlling at least one of the following reaction conditions for the second reaction zone: its temperature profile, the rate at which at least one reactant is introduced therein through its inlet, and the rate at which at least one reaction product is expelled therefrom through its outlet, wherein at least one of said reaction conditions associated with the first reaction zone is capable of being controlled independently of the corresponding reaction condition associated with the second reaction zone; and
   c. an analyzing system for analyzing at least one reaction product expelled from the first or second reaction zones to determine at least one of the following: at least one physical property of said reaction product, at least one chemical property of said reaction product, at least one performance property of a reactant used in producing a reaction product, at least one of the effects of any one or more reaction conditions on a reaction product, and at least one of the effects of any one or more reaction conditions on at least one performance property of any reactant used in producing a reaction product.

12. The system of claim 11 wherein said first and second reaction zones comprise a reaction tube.

13. The system of claim 11 wherein said first controlling system and said second controlling system are the same.

14. The system of claim 11 wherein said first and second controlling systems are in communication with input controls that are in fluid communication with each of said first and second reaction zones for separately controlling the rate at which at least one reactant is introduced in said first and second reaction zones, and the rate at which at least one reaction product is expelled therefrom.

15. The system of claim 14 wherein said input controls comprise one or more of the following: a reactant feed source, a mass flow controller, and a moisture controller.

16. The system of claim 11 wherein said first and second controlling systems are in communication with a heating element that is in thermal communication with each of said first and second reactions zones for controlling the temperature profile of each of said first and second reaction zones.

17. The system of claim 11, further comprising a first reactor core for housing said first reaction zone and a second reactor core for housing said second reaction zone.

18. The system of claim 17, wherein said first and second reactor cores comprise an input manifold and an output manifold and wherein said inlet of each of said first and second reaction zones is positioned in said input manifold and said outlet of each of said first and second reaction zones is positioned in said outlet manifold.

19. The system of claim 17 further comprising a first reaction zone selector valve for selectively routing the reaction product expelled from said first reaction zone in response to a communication from said first controlling system and a second reaction zone selector valve for selectively routing the reaction product expelled from said second reaction zone in response to a communication from said second controlling system.

20. The system of claim 19, further comprising a reactor core selector valve for selectively routing the reaction product from one of said first reaction zone selector valve and said second reaction zone selector valve to said analyzing system in response to a communication from said first or second controlling system.

21. The system of claim 11, wherein said analyzing system comprises at least one device to analyze at least one of said reaction products which is selected from the group consisting of spectroscopic detection devices and chromatographic detection devices.

* * * * *